United States Patent [19]

Belgard et al.

[11] 4,349,030

[45] Sep. 14, 1982

[54] EXTERNAL NONINVASIVE ELECTRIC CARDIAC STIMULATION

[75] Inventors: Alan H. Belgard, Sharon; Paul M. Zoll, Newton Centre, both of Mass.; Ross H. Zoll, 261 Brookline St., Newton Centre, Mass. 02159

[73] Assignee: Ross H. Zoll, Newton Centre, Mass.

[21] Appl. No.: 168,381

[22] Filed: Jul. 10, 1980

[51] Int. Cl.³ .............................................. A61N 1/36

[52] U.S. Cl. .............................................. 128/419 PG

[58] Field of Search ............... 128/639, 697, 798, 802, 128/803, 419 D, 419 PG, 421, 422

[56] References Cited

U.S. PATENT DOCUMENTS

| | | | |
|---|---|---|---|
| 3,077,884 | 2/1963 | Batrow et al. | 128/802 |
| 3,258,013 | 6/1966 | Druz | 128/419 D |
| 3,716,059 | 2/1973 | Welborn et al. | 128/419 D |
| 3,762,420 | 10/1973 | Moore et al. | 128/419 D |
| 4,014,347 | 3/1977 | Halleck et al. | 128/422 |
| 4,207,904 | 6/1980 | Greene | 128/798 |

FOREIGN PATENT DOCUMENTS

| | | | |
|---|---|---|---|
| 864362 | 4/1961 | United Kingdom | 128/419 D |

OTHER PUBLICATIONS

Cooley, "Annals of Surgery", vol. 132, No. 5, Nov. 1950, pp. 934–935.

Patel et al., "Proceedings of 23rd Annual Conference on Engineering in Medicine & Biology", Wash., D.C., 16–19 Nov. 1970, p. 27.

Zoll et al., "AMA Archives of Internal Medicine", vol. 96, Nov. 1955, pp. 639–653.

Zoll, "The New England Journal of Medicine", 13 Nov. 1952, pp. 768–771.

Zoll et al., "Annals of the N. Y. Academy of Sciences", vol. 111, pp. 932–937, 11 Jun. 1964.

Jongs et al., "Cardiovascular Research Center Bulletin", Apr.–Jun. 1977, pp. 101–112.

Electreat, Inc. Catalog, 4 pp. only information available.

*Primary Examiner*—William E. Kamm

[57] ABSTRACT

Reducing pain from external noninvasive electric cardiac stimulation through the use of electrodes with large-surface, non-metallic, skin-contacting members providing low current density, and also through the use of a pulse generator for the electrodes that provides constant current without spikes throughout a prolonged pulse of greater than 5 milliseconds duration.

22 Claims, 3 Drawing Figures

FIG 1
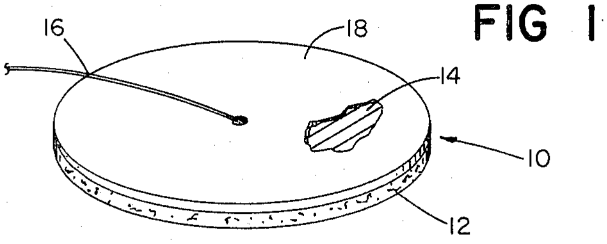
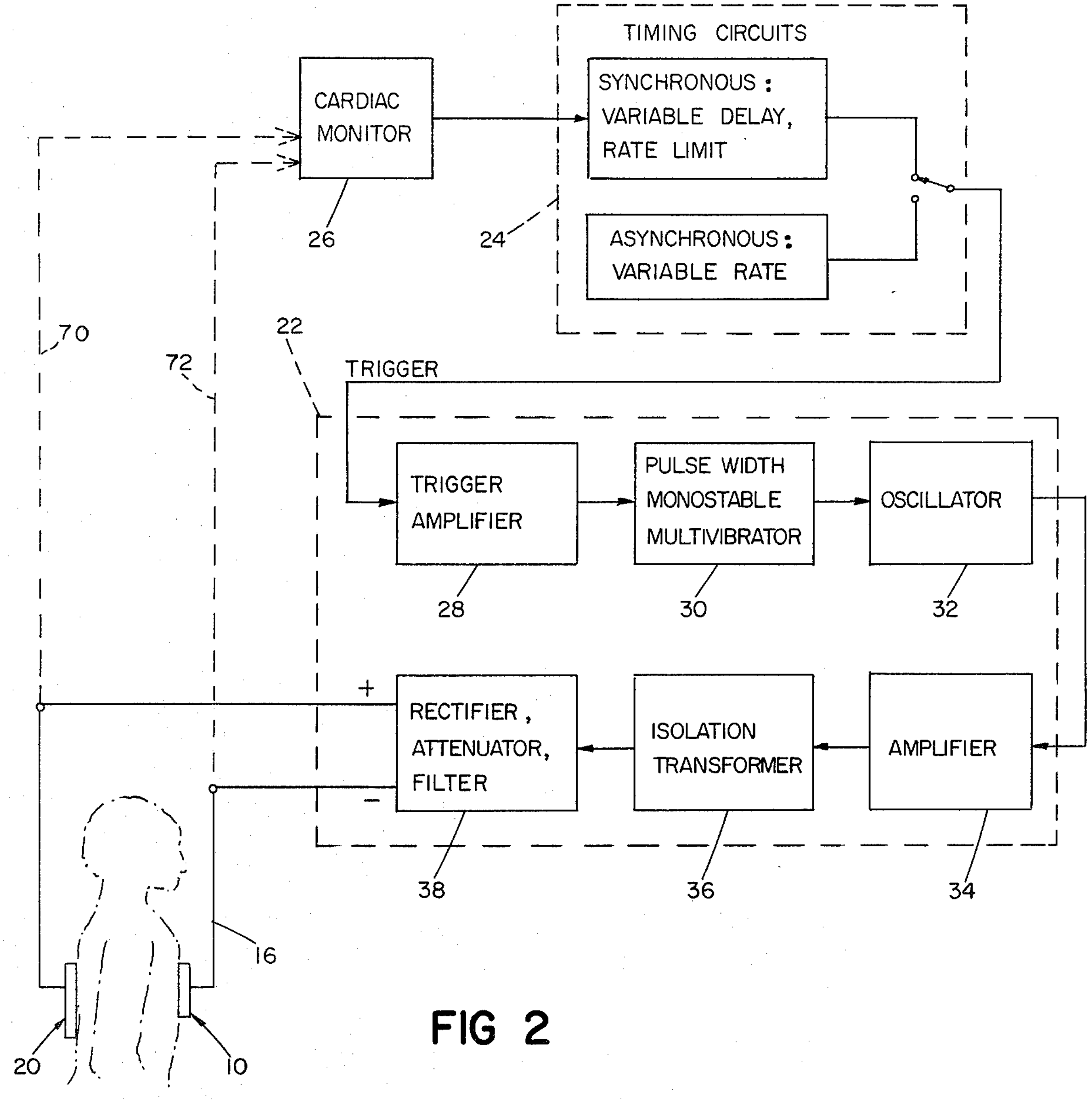
FIG 2 through transformer 36, it is first converted by oscillator 32 to a 2 Kc square wave, which is then rectified and filtered after passing through the transformer. The output of multivibrator 30 is connected to oscillator 32 through inverter $I_4$. Oscillator 32 comprises gates $G_2$, $G_3$ and inverter $I_5$ and has two output nodes 50, 52, with outputs 180 degrees out of phase with each other. Node 52 is connected to inverter $I_5$, and node 50 is connected to the oscillator 32 through gate $G_4$.

Referring to the upper part of FIG. 3, a regulated 24-volt supply is provided between nodes 54, 56 by batteries 41, capacitor 58, voltage regulator 60, and transistor $T_1$. Amplifier 34 provides identical amplification to the out-of-phase signals at nodes 50, 52 by transistors $T_2$, $T_3$, $T_4$ and $T_5$. These amplified signals are connected, along with the 24-volt regulated supply, to the primary windings of 10:1 step-up and isolation transformer 36. The secondary windings of transformer 36 are connected to rectifier 59, which is connected to the electrodes 10, 20 through potentiometer 62 (5 Kohms, 5 W) and filter 64, comprising a capacitor and inductor 66 (a transformer coil with an iron core, inductance ⅓ H). Filter 64 acts to produce a smooth current pulse of sufficiently uniform amplitude, its inductance eliminating initial transient current spikes caused by capacitance of electrodes 10, 20.

The following table contains the circuit components used in the circuitry shown in FIG. 3.

| Component Table | |
|---|---|
| $I_1$, $I_2$, $I_4$, $I_5$ | 4069 |
| $G_1$, $G_2$, $G_3$, $G_4$ | 4001 |
| $T_1$, $T_3$, $T_5$ | 2N 1724 |
| Regulator 60 | LM 340 |
| $T_2$, $T_4$ | 2N 2108 |
| Diodes 46 | Texas Instruments 59 |
| $D_1$, $D_2$ | 1N 4000 |
| Rectifier 59 | Motorola R0804 |

OPERATION

In operation sponge 12 (and the corresponding sponge on electrode 20) are first dampened with tap water; alternatively, a weak electrolyte, such as sodium bicarbonate, or a gel may be used on the sponges. The electrodes 10, 20 provide low current density. The dampness or the gel provides good electrical contact with the patient's skin over a wide area without decreasing the resistance of the electrode too much. Electrodes 10, 20 are positioned on the patient's chest (near the heart at the left parasternal fourth or fifth interspace) and back (subscapular, i.e., below the shoulder blade), respectively, to reduce muscle stimulation. When emergency resuscitation from ventricular standstill or bradycardia is provided, the timing circuitry 24 will be in the asynchronous mode, and stimuli will be provided at an adjustable uniform rate of 30 to 200 per minute. When the synchronous mode of circuitry 24 is used (e.g., during physiological testing), the stimulus is produced at a uniform adjustable delay following the QRS synchronizing signal from cardiac monitor 26. Regardless of which mode the timing circuitry 24 is in, pulse generator 22 will provide the same uniform pulse for each trigger signal inputted.

Potentiometer 62 acts as an adjustable amplitude control and accommodates the various thresholds of individual patients. The maximum output pulse to the patient is 140 milliamps into 2,000 ohms, with a 500 ohm source impedance.

A pulse width greater than 20 ms is used to reduce current required for cardiac stimulation to more comfortable levels.

OTHER EMBODIMENTS

Resistor 48 can be replaced with a potentiometer to vary the pulse width, e.g., between 2–40 ms. Other nonmetal members such as gauze can be used instead of sponge 12.

Also, although the 8 cm and 12 cm diameters for the electrodes are optimal for the average adult, they can be varied between 6 and 10 cm and 8 and 15 cm, respectively, to accommodate different patient's sizes and relative sensitivities to nerve stimulation and muscle contraction. (Increases in electrode diameter reduce nerve stimulation but increase the amount of muscle which can be contracted and vice versa.)

Finally, instead of using separate electrodes for the cardiac monitor 26, a heart beat signal can be obtained directly from the stimulating electrodes 10, 20 as is indicated by dashed lines 70, 72.

What is claimed is:

1. An external noninvasive electric cardiac stimulation system comprising a pair of electrodes having nonmetallic skin-contacting members that provide low current density to reduce stimulation of local sensory nerves and resulting pain, a pulse generator electrically connected to said electrodes, said generator including means to provide constant current pulses without high current spikes that cause skeletal muscle contraction, said pulses being greater than 5 milliseconds in duration to reduce the threshold current required for cardiac stimulation, to permit the use of lower current pulses to provide effective stimulation at the same time that skeletal muscle contraction is reduced by the lower current, and means to activate said pulse generator to provide said current pulses.

2. The system of claim 1 wherein said generator includes an inductor to eliminate transient current spikes from charges on the electrodes.

3. The system of claim 2 further comprising means for varying the duration of said pulses.

4. The system of claim 3 wherein said pulse duration is between 20 and 40 milliseconds.

5. The system of claim 4, further comprising means to vary the amplitude of said pulse.

6. The system of claim 1 wherein said electrodes are circular, one said electrode having a diameter between 6 and 10 centimeters, the other said electrode having a diameter between 8 and 15 centimeters.

7. The system of claim 6 wherein each said electrode further comprises a metal disc adhered to the non-skin-contacting surface of said member and an insulating material covering the exposed surfaces and edges of said metal disc, and further comprising a pair of electrical wires, and wherein each said electrode is electrically connected to said pulse generator by a said electrical wire electrically connected to a said metal disc and said pulse generator.

8. The system of claim 7 wherein said metal disc is made from stainless steel.

EXTERNAL NONINVASIVE ELECTRIC CARDIAC STIMULATION

FIELD OF THE INVENTION

This invention relates to external cardiac stimulation.

BACKGROUND OF THE INVENTION

External electric stimulation is a well-established noninvasive technique that provides effective heart beats in emergency resuscitation of patients from ventricular standstill. However, the pain caused by external electric stimulation of conscious patients has inhibited its widespread use in temporary cardiac stimulation. The presently most widely used technique for temporary cardiac stimulation involves the invasive procedure of cardiac catheterization, wherein a temporary electrode wire is placed in the heart.

SUMMARY OF THE INVENTION

It has been discovered that the severe pain from stimulation of local sensory nerves during external electric cardiac stimulation can be largely eliminated by the use of electrodes with large-surface, non-metallic, skin-contacting members providing low current density. It has also been discovered that the discomfort from strong contractions of skeletal muscles near the electrodes can be reduced through the use of an electrical pulse generator that provides a constant current output and thereby eliminates the high-current spikes which cause skeletal muscle contractions without affecting cardiac stimulation. It has also been discovered that by increasing the stimulus pulse duration from 2 milliseconds (ms) to 5 to 40 ms, the current required for cardiac stimulation is reduced approximately 30 to 50% without increasing skeletal muscle contraction. Accordingly, the invention features the production of external electric cardiac stimulation with electrodes with large-surface, non-metallic, skin-contacting members providing low current density and a pulse generator that provides the electrodes with a constant current pulse of greater than 5 milliseconds (preferably 20 to 40 milliseconds) duration. In preferred embodiments inductance is provided near the electrodes to eliminate transient current spikes; means to allow for variations in pulse duration are provided; a potentiometer is provided near the electrode connections to vary the amplitude of the pulse; the diameters of the skin-contacting members are between 6 and 10 cm for the anterior electrode and between 8 and 15 cm for the posterior electrode; the electrodes are made of a thin metal disc attached on one side to the non-metallic skin-contacting member and connected on the other side to a wire lead; the skin-contacting member is a sheet of cellulose sponge approximately ¼" in thickness; the disc is made of stainless steel; and the disc is covered with a silicon rubber insulating material on the side to which the electrical connection is made.

DESCRIPTION OF THE PREFERRED EMBODIMENT

The structure and operation of the presently preferred embodiment will be described after first briefly describing the drawings.

DRAWINGS

FIG. 1 is a diagrammatic perspective view, partially broken away, of an electrode according to the invention.

FIG. 2 is a block diagram showing the electrodes connected to a pulse generator, which is in turn connected to a cardiac monitor and timing circuits.

STRUCTURE

Figure 3:
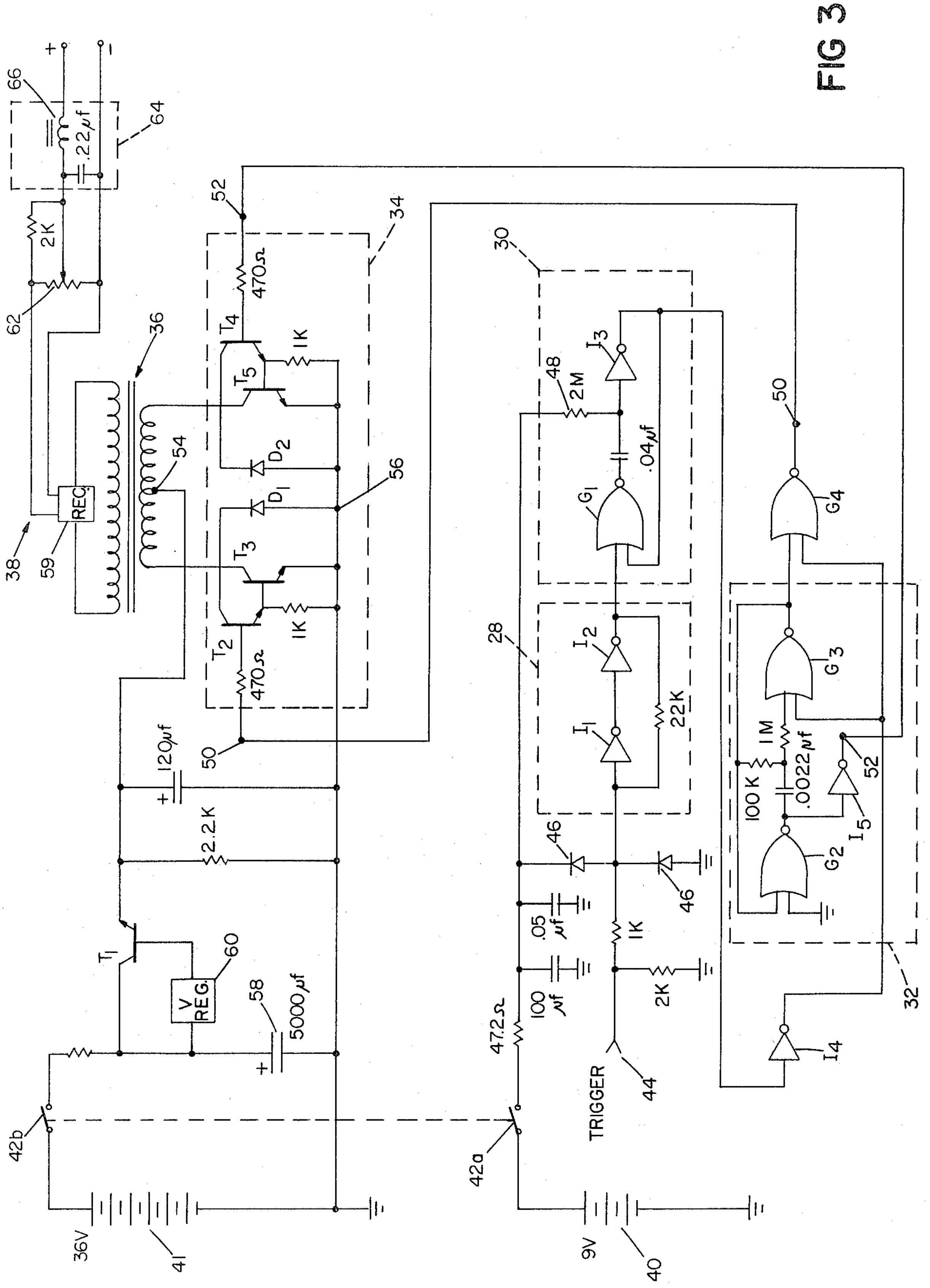
FIG. 3 is a schematic for the pulse generator circuitry.

There is shown in FIG. 1 an 8 cm diameter anterior electrode 10 made of ¼" thick cellulose sponge 12 attached to one surface of thin stainless steel disc 14, which is electrically connected to insulated wire 16 and covered on its other surface by silicone rubber insulator layer 18, the insulator layer also covering the edges of plate 14. The posterior electrode 20 (not shown in FIG. 1) is identical to electrode 10 except that it is 12 cm in diameter.

Referring to FIG. 2, the electrodes are shown attached to a patient's chest and electrically connected to pulse generator 22. The input for pulse generator 22 is a trigger signal (approximately 10 volts) provided by timing circuitry 24, which is of a type well known in the art. In a synchronous mode QRS signals of the heart beats from standard cardiac monitor 26 control the trigger signal; in an asynchronous mode the trigger signals are provided at an adjustable uniform rate; a switch (not shown) also permits the operator to trigger signals manually; and finally, means for generating single or multiple signals in any complex timing pattern desired is provided. An adjustable rate limit control in the synchronous mode prevents rapid stimulation of frequency QRS synchronizing signals, and it also allows the production of stimuli only after alternate or after three or more QRS synchronizing signals. Pulse generator 22, which will be discussed in detail below, generally comprises trigger amplifier 28, pulse width monostable vibrator 30, oscillator 32, amplifier 34, isolation transformer 36, and output circuitry 38, comprising a rectifier, attenuator and filter.

There is shown in FIG. 3 the circuitry for pulse generator 22. The lower half of the figure presents CMOS logic elements, which are used to control the output stages, and the upper half of the figure presents the output stages, comprising amplifier 34, transformer 36 and output circuitry 38 along with their regulated voltage source. The CMOS logic elements are powered by 9-volt battery 40, and the output stages are powered by six 6-volt lantern batteries generally indicated 41 and connected in series to achieve 36 volts. The pulse generator 22 has mechanically-connected on/off controls 42 (*a*) and (*b*) for the CMOS logic elements and the output stages, respectively.

Referring to the lower part of FIG. 3, the trigger signal enters at node 44. Diodes 46 protect the trigger input. Trigger amplifier 28 is used to provide sharp transition for the trigger signal and comprises inverters $I_1$, $I_2$, which are connected in a positive feedback loop. One-shot pulse width monostable multivibrator 30 comprises NOR gate $G_1$, inverter $I_3$, resistor 48 and a capacitor. Its output is a uniform fixed-width pulse. With the specific capacitor and resistor shown in FIG. 3, as 40 ms pulse is generated. To protect the patient from leakage currents and component failures, the output to the patient is transformer-coupled. To pass the 40 ms pulse 9. The system of claim 8 wherein said member is made of cellulose sponge material.

10. The system of claim 9 wherein said insulating material is silicone rubber.

11. The system of claim 8 wherein said members are made of gauze.

12. The system of claim 1 wherein said means to activate includes a cardiac monitor and means to provide triggers for said pulse generator in response to the electrical output of said cardiac monitor, said means to provide triggers being adapted to synchronize said triggers to occur in a desired phase relation with the heart beat.

13. The system of claim 12 wherein said electrodes provide input to said cardiac monitor.

14. A method for providing external noninvasive electric cardiac stimulation comprising attaching two electrodes to a patient's chest, said electrodes having nonmetallic skin-contacting members providing low current density to reduce stimulation of local sensory nerves, and sending electric pulses between said electrodes, said pulses having constant current without high current spikes that cause skeletal muscle contraction and being of greater than 5 milliseconds duration to reduce the threshold current required for cardiac stimulation, to permit the use of lower current pulses to provide effective stimulation at the same that skeletal muscle contraction is reduced at the lower current.

15. The method of claim 14 wherein said pulse duration is between 20 and 40 milliseconds.

16. The method of claim 14 wherein said pulses are provided by a pulse generator having means to vary the amplitude of said pulse and further comprising prior to said sending step, adjusting the amplitude of the pulse to a desired level depending upon the physical characteristics of said patient.

17. The method of claim 14 wherein said members are sponges dampened with tap water.

18. The method of claim 14 wherein said members are made of gauze.

19. The method of claim 14 wherein one said electrode is attached to the front of the patient's chest and the other said electrode is attached to the back of the patient's chest.

20. The method of claim 19 wherein said one electrode has a diameter between 6 and 10 centimeters and said another electrode has a diameter between 8 and 15 centimeters.

21. The method of claim 14 wherein said members are sponges dampened with a weak electrolyte.

22. The method of claim 14 wherein said sponges are covered with a gel.

* * * * *